(12) United States Patent
Cooper et al.

(10) Patent No.: US 10,675,283 B2
(45) Date of Patent: Jun. 9, 2020

(54) COMPOSITIONS AND METHODS FOR WHITE TO BEIGE ADIPOGENESIS

(71) Applicants: Denise Ratzlaff Cooper, St. Petersburg, FL (US); Ryan Adam Kirchoffer, Ocala, FL (US); Robert Pleasants Sparks, Urbana, IL (US); Wayne Charles Guida, Saint Pete Beach, FL (US)

(72) Inventors: Denise Ratzlaff Cooper, St. Petersburg, FL (US); Ryan Adam Kirchoffer, Ocala, FL (US); Robert Pleasants Sparks, Urbana, IL (US); Wayne Charles Guida, Saint Pete Beach, FL (US)

(73) Assignees: University of South Florida, Tampa, FL (US); The United States Government as Represented by the Department Of Veterans Affairs, Washington, DC (US)

( * ) Notice: Subject to any disclaimer, the term of this patent is extended or adjusted under 35 U.S.C. 154(b) by 0 days.

(21) Appl. No.: 15/936,326

(22) Filed: Mar. 26, 2018

(65) Prior Publication Data
US 2018/0271867 A1    Sep. 27, 2018

Related U.S. Application Data

(60) Provisional application No. 62/476,199, filed on Mar. 24, 2017.

(51) Int. Cl.
| | | |
|---|---|---|
| *A61K 31/517* | (2006.01) | |
| *A61P 3/04* | (2006.01) | |
| *A61K 31/473* | (2006.01) | |

(52) U.S. Cl.
CPC .......... *A61K 31/517* (2013.01); *A61K 31/473* (2013.01); *A61P 3/04* (2018.01)

(58) Field of Classification Search
CPC .................................................. A61K 31/517
See application file for complete search history.

(56) References Cited

U.S. PATENT DOCUMENTS

| | | | |
|---|---|---|---|
| 4,554,101 A | 11/1985 | Hopp | |
| 5,580,859 A | 12/1996 | Felgner et al. | |
| 5,679,647 A | 10/1997 | Carson et al. | |
| 5,703,055 A | 12/1997 | Felgner et al. | |
| 2005/0288347 A1 | 12/2005 | Hodge et al. | |

FOREIGN PATENT DOCUMENTS

| | | |
|---|---|---|
| WO | WO 2006/012577 A2 | 2/2006 |
| WO | WO 2008/110598 A1 | 9/2008 |

OTHER PUBLICATIONS

C.T.F.A. Cosmetic Ingredient Handbook, 1992, pp. 587-592.
Donnelly et al., "DNA Vaccines," Ann. Rev. Immunol., 1997, 15: 617-648.
Harms et al., "Brown and beige fat: development, function and therapeutic potential," Nat Med, 2013, 19(10):1252-63.
Heagerty et al., "Time-dependent ROC curves for censored survival data and a diagnostic marker," Biometrics, 2000, 56(2):337-344.
IUPAC, "Rules for the Nomenclature of Organic Chemistry, Section E: Stereochemistry, Recommendations 1974," Pure Appl. Chem., 1976, 45: 13-30.
Kyte et al., "A Simple Method for Displaying the Hydropathic Character of a Protein," J. Mol. Biol. 1982, 157, 105-132.
Li et al., "Clk/STY (cdc2-Like Kinase 1) and Akt Regulate Alternative Splicing and Adipogenesis in 3T3-L1 Pre-Adipocytes," PLoS One, 2013, 8(1): e53268.
McCutcheon's vol. 1, Emulsifiers & Detergents, 1994, North American Edition, pp. 236-239.
Mott et al., "Evaluation of substituted 6-arylquinazolin-4-amines as potent and selective inhibitors of cdc2-like kinases (Clk)," Bioorganic & Medicinal Chemistry Letters, 2009, 19(23): 6700-6705.
National Center for Biotechnology Information, PubChem Compound Database, CID=1078896, <https://pubchem.ncbi.nlm.nih.gov/compound/1078896> Created date: Jul. 10, 2005.
National Center for Biotechnology Information, PubChem Compound Database, CID=6796626, <https://pubchem.ncbi.nlm.nih.gov/compound/6796626> Created date: Jun. 6, 2006.
Patel et al., "Clk: A switch for beginning of de novo differentiating 3T3-L1 pre-adipocytes," Poster presented at USF Research Day, Feb. 2017.
Rao et al., "Synthesis and Biological Evaluation of Novel Bouchardatine Derivatives as Potential Adipogenesis/Lipogenesis Inhibitors for Antiobesity Treatment," J Med Chem, 2015, 58(23): 9395-9413.
Remington's Pharmaceutical Sciences, 15th Ed. 1975, pp. 335-337.
Wang et al., "Resveratrol induces brown-like adipocyte formation in white fat through activation of AMP-activated protein kinase (AMPK) α1," Int J Obes, 2015, 39(6):967-76.
Wu et al., "Beige adipocytes are a distinct type of thermogenic fat cell in mouse and human," Cell, 2012, 150, 366-376.

*Primary Examiner* — Paul V Ward
(74) *Attorney, Agent, or Firm* — Fish & Richardson P.C.

(57) ABSTRACT

Disclosed herein are compositions and methods for transitioning or converting a white adipocyte to a beige adipocyte. The compositions and methods may be used in the treatment of obesity. In some embodiments, the compositions include a compound selected from DC677 and DC761.

3 Claims, 5 Drawing Sheets

FIGURES

COMPOSITIONS AND METHODS FOR WHITE TO BEIGE ADIPOGENESIS

CROSS-REFERENCE TO RELATED APPLICATION(S)

This application claims priority to U.S. Provisional Patent Application No. 62/476,199, filed Mar. 24, 2017, which is incorporated herein by reference in its entirety.

FIELD

This disclosure relates to compositions for white to beige adipogenesis and methods of using the same, which may be used to treat or prevent obesity.

INTRODUCTION

Obesity and its associated disorders are common and very serious public health problems in the United States and throughout the world. The worldwide medical cost of obesity and associated disorders is enormous. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease.

Obesity develops when energy intake chronically exceeds total energy output. Fat tissue in obesity results from adipocyte hyperplasia or the formation of new adipocytes from progenitors, and from hypertrophy (enlargement) of pre-existing adipocytes. Obesity remains a chronic, essentially intractable, metabolic disorder with few treatment options available. A need exists for new therapies useful in treating obesity and/or adipogenesis.

SUMMARY

In an aspect, the disclosure relates to methods of inhibiting Clk1 in a subject in need thereof. The method may include administering to the subject a compound selected from the following:

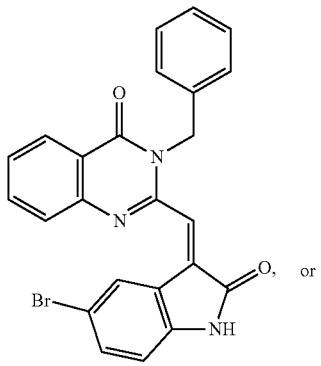
DC677

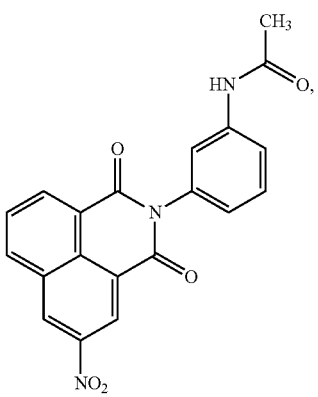
DC761 or a pharmaceutically acceptable salt thereof, or a combination thereof.

In a further aspect, the disclosure relates to methods of reducing or treating obesity in a subject. The method may include administering to the subject a compound selected from the following:

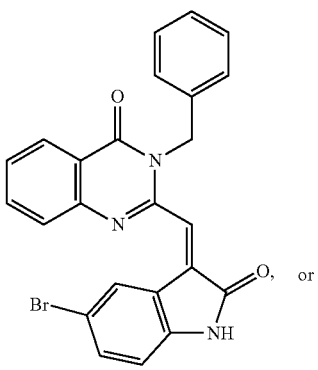
DC677

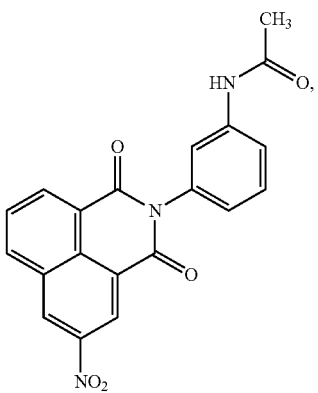
DC761 or a pharmaceutically acceptable salt thereof, or a combination thereof.

Another aspect of the disclosure provides methods of reducing body mass index (BMI) in a subject. The method may include administering to the subject a compound selected from the following:

DC677

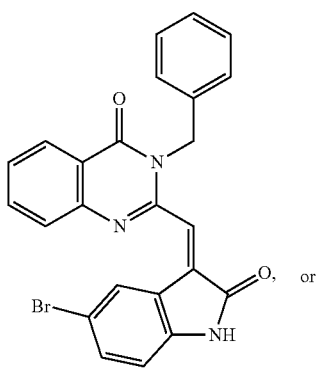

DC761

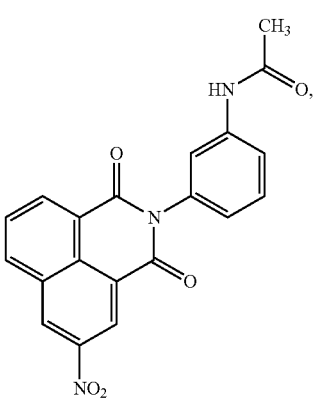

or a pharmaceutically acceptable salt thereof, or a combination thereof.

In some embodiments, the compound comprises the following:

DC677

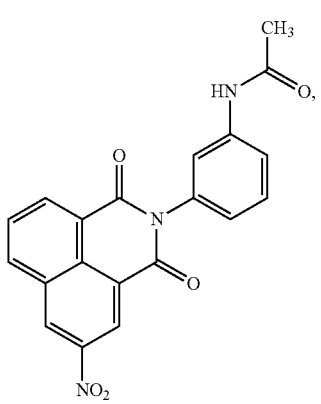

DC677

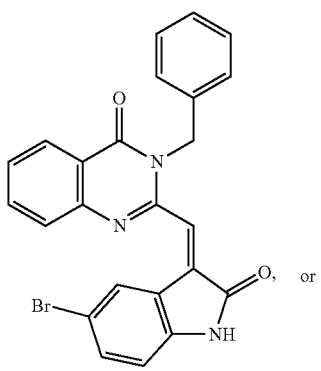

or

In some embodiments, the compound comprises the following:

DC761

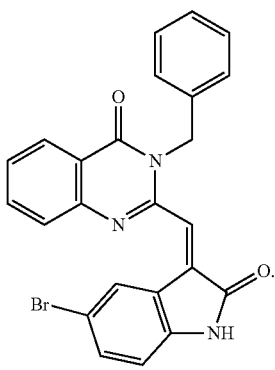

In some embodiments, the compound comprises the following:

DC761

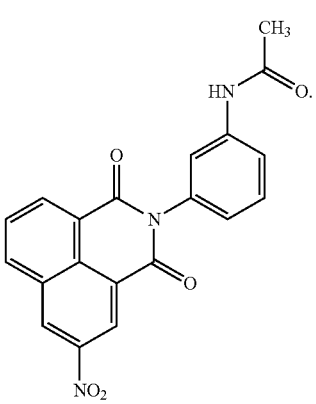

In some embodiments, the compound or salt inhibits Clk1. In some embodiments, the compound or salt does not inhibit Clk2, Clk3, or Clk4, or a combination thereof. In some embodiments, the compound or salt binds to Clk1. In some embodiments, alternative splicing of protein kinase C beta 1 (PKCβ1) is reduced relative to a control. In some embodiments, the lipid droplets of the adipocytes in the subject are reduced in size relative to a control. In some embodiments, the adipocytes in the subject store less lipids relative to a control. In some embodiments, the expression of UCP1 in the subject is increased relative to a control. In some embodiments, the expression of PGCα in the subject is increased relative to a control. In some embodiments, the expression levels of UCP1 and PGCα in the subject are increased relative to a control. In some embodiments, the control comprises white adipocytes. In some embodiments, the control comprises a sample from the subject prior to administration of the compound.

Another aspect of the disclosure provides a pharmaceutical composition comprising a compound selected from the following:

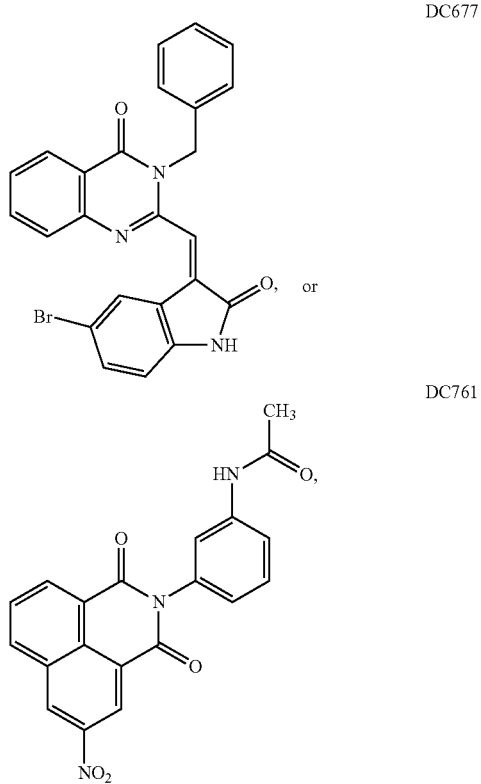 [SMILES: O=C1Nc2ccc(Br)cc2/C1=C\c1nc2ccccc2c(=O)n1Cc1ccccc1 ; CC(=O)Nc1cccc(N2C(=O)c3cccc4cc([N+](=O)[O-])cc(c34)C2=O)c1]

or
a pharmaceutically acceptable salt thereof, or a combination thereof, and a carrier.

In some embodiments, the compound or salt inhibits Clk1. In some embodiments, the compound or salt does not inhibit Clk2, Clk3, or Clk4, or a combination thereof.

The disclosure provides for other aspects and embodiments that will be apparent in light of the following detailed description and accompanying figures.

BRIEF DESCRIPTION OF THE DRAWINGS

FIG. 1A is a graph of the relative expression of UCP1 in 3T3-L1 cells cultured in the presence of TG003 or DC677. FIG. 1B is a graph of the relative expression of PGC1α in 3T3-L1 cells cultured in the presence of TG003 or DC677. FIG. 1C is a graph of the absorbance at 520 nm of 3T3-L1 cells cultured in the presence of TG003 or DC677 and stained with Oil Red O. FIG. 1D is a graph of the absorbance at 495 nm of 3T3-L1 cells cultured in the presence of TG003 or DC677 and stained with MitoTracker™ Green (Thermo Fischer Scientific, Waltham, Mass.).

FIG. 2A is a graph of the relative expression of UCP1 in 3T3-L1 cells cultured in the presence of TG003, DC677, or DC761. FIG. 2B is a graph of the relative expression of PGC1α in 3T3-L1 cells cultured in the presence of TG003, DC677, or DC761. FIG. 2C is a graph of the absorbance at 520 nm of 3T3-L1 cells cultured in the presence of TG003, DC677, or DC761 and stained with Oil Red O. FIG. 2D is a graph of the absorbance at 495 nm of 3T3-L1 cells cultured in the presence of TG003, DC677, or DC761 and stained with MitoTracker™ Green (Thermo Fischer Scientific, Waltham, Mass.).

DETAILED DESCRIPTION

Figure 1A:
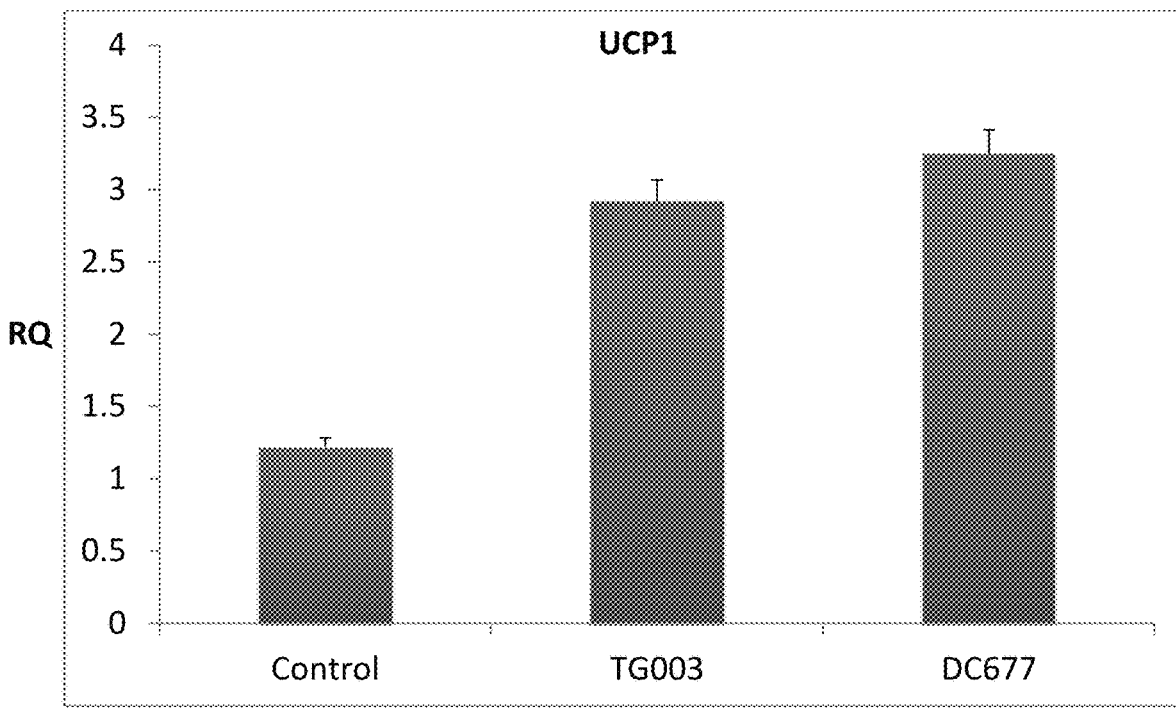
FIG. 1A, FIG. 1B, FIG. 1C, and FIG. 1D are graphs showing the effect of TG003 or DC677 on 3T3-L1 cells.

Described herein are compositions and methods for converting a white adipocyte to a beige adipocyte. It was discovered that the compounds detailed herein alter the characteristics of a white adipocyte such that it becomes more like a brown adipocyte. The compounds may convert white adipocytes to beige adipocytes. The compounds may be used in methods to treat or reduce obesity. The methods may include the stimulation of beige adipocytes within white adipose tissue (WAT) to dissipate chemical energy. These methods may involve induction of peroxisome proliferator-activated receptor gamma co-activator-1-alpha (PGC1α), uncoupling protein 1 (UCP1), and other genes involved in mitochondrial biogenesis.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 7$^{th}$ Edition, John Wiley & Sons, Inc., New York, 2013; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" or "alkoxyl" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 20 carbon atoms. The term "lower alkyl" or "$C_1$-$C_6$ alkyl" means a straight or branched chain hydrocarbon containing from 1 to 6 carbon atoms. The term "$C_1$-$C_4$ alkyl" means a straight or branched chain hydrocarbon containing from 1 to 4 carbon atoms. The term "$C_1$-$C_3$ alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkoxyalkyl" as used herein, refers to an alkoxy group, as defined herein, appended to the parent molecular moiety through an alkylene group, as defined herein.

The term "arylalkyl" as used herein, refers to an aryl group, as defined herein, appended to the parent molecular moiety through an alkylene group, as defined herein.

The term "alkylamino," as used herein, means at least one alkyl group, as defined herein, is appended to the parent molecular moiety through an amino group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino" as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl" as used herein, refers to an aromatic group such as a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl, and tetrahydroquinolinyl.

The term "carboxyl" as used herein, means a carboxylic acid, or —COOH.

The term "cycloalkyl" means a monovalent saturated hydrocarbon ring or a bicyclic group. Cycloalkyl groups have zero heteroatoms and zero double bonds. Cycloalkyl groups are monocyclic, or are fused, spiro, or bridged bicyclic ring systems. Monocyclic cycloalkyl groups contain 3 to 10 carbon atoms, preferably 4 to 7 carbon atoms, and more preferably 5 to 6 carbon atoms in the ring. Bicyclic cycloalkyl groups contain 8 to 12 carbon atoms, preferably 9 to 10 carbon atoms in the ring. Cycloalkyl groups may be substituted or unsubstituted. Cycloalkyl groups include, for example, cyclopropyl, cyclobutyl, cyclopentyl, cyclohexyl, and cycloheptyl.

The term "cycloalkenyl," as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl, and cycloheptenyl.

The term "cycloalkynyl," as used herein, means a monocyclic or multicyclic ring system containing at least one carbon-carbon triple bond and preferably having from 5-10 carbon atoms per ring or more than 10 carbon atoms per ring.

The term "haloalkyl" as used herein, means an alkyl group, as defined herein, in which one, two, three, four, five, six, seven or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" or "halo" as used herein, means Cl, Br, I, or F.

The term "heteroalkyl" as used herein, means an alkyl group, as defined herein, in which at least one of the carbons of the alkyl group is replaced with a heteroatom, such as oxygen, nitrogen, and sulfur. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system containing at least one heteroatom independently selected from the group consisting of N, O, and S. The aromatic monocyclic rings are five or six membered rings containing at least one heteroatom independently selected from the group consisting of N, O, and S. The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic" or "heterocyclyl" as used herein means a monocyclic heterocycle, a bicyclic heterocycle (heterobicyclic), or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroarylalkyl" as used herein, refers to a heteroaryl group, as defined herein, appended to the parent molecular moiety through an alkylene group, as defined herein.

The term "heterocyclylalkyl" as used herein, refers to a heterocycle group, as defined herein, appended to the parent molecular moiety through an alkylene group, as defined herein.

The term "hydroxyl" or "hydroxy" as used herein, means an —OH group.

The term "hydroxyalkyl" as used herein, means at least one —OH group, is appended to the parent molecular moiety through an alkylene group, as defined herein.

The term "nitro" means a —NO$_2$ group.

In some instances, the number of carbon atoms in a hydrocarbyl substituent (e.g., alkyl or cycloalkyl) is indicated by the prefix "$C_x$-$C_y$—", wherein x is the minimum and y is the maximum number of carbon atoms in the substituent. Thus, for example, "$C_1$-$C_3$ alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "administration" or "administering," as used herein, refers to providing, contacting, and/or delivery of a compound by any appropriate route to achieve the desired effect. These compounds may be administered to a subject in numerous ways including, but not limited to, orally, ocularly, nasally, intravenously, topically, as aerosols, suppository, etc. and may be used in combination.

The term "agonist" refers to a biologically active ligand that binds to its complementary biologically active receptor and activates the receptor either to cause a biological response in the receptor or to enhance a biological activity of the receptor. An agonist may trigger (e.g., initiate or promote), partially or fully enhance, stimulate, or activate one or more biological activities. An agonist may mimic the action of a naturally occurring substance.

"Antagonist" or "inhibitor" refers to an agent that inhibits the effect of an agonist. An antagonist may be a compound that inhibits or reduces an activity of a polypeptide. An antagonist may indirectly or directly bind a polypeptide and inhibit the activity of the polypeptide, including binding activity or catalytic activity. For example, an antagonist may prevent expression of a polypeptide, or inhibit the ability of a polypeptide to mediate the binding of the polypeptide to a ligand. An "allosteric antagonist" refers to a compound that binds to a polypeptide at a secondary site, distinct from the primary ligand binding site, and inhibits or reduces an activity of the polypeptide.

The terms "inhibit" or "inhibiting" mean that an activity is decreased or prevented in the presence of an inhibitor as opposed to in the absence of the inhibitor. The term "inhibition" refers to the reduction or down regulation of a process or the elimination of a stimulus for a process, which results in the absence or minimization of the expression or activity of a biomolecule or polypeptide. Inhibition may be direct or indirect. Inhibition may be specific, that is, the inhibitor inhibits a biomolecule or polypeptide and not others.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject or cell without a compound as detailed herein. A control may be a subject, or a sample therefrom, whose disease state is known. The subject, or sample therefrom, may be healthy, diseased, diseased prior to treatment, diseased during treatment, or diseased after treatment, or a combination thereof. The term "normal subject" as used herein means a healthy subject, i.e. a subject having no clinical signs or symptoms of disease. The normal subject is clinically evaluated for otherwise undetected signs or symptoms of disease, which evaluation may include routine physical examination and/or laboratory testing. In some embodiments, the control is a healthy control.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Sample" or "test sample" as used herein can mean any sample in which the presence and/or level of a target or activity is to be detected or determined or any sample comprising a compound as detailed herein. Samples may include liquids, solutions, emulsions, or suspensions.

Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, adipose tissue, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

The term "specificity" as used herein refers to the number of true negatives divided by the number of true negatives plus the number of false positives, where specificity ("spec") may be within the range of 0<spec<1. Ideally, the methods described herein have the number of false positives equaling zero or close to equaling zero, so that no subject is wrongly identified as having a disease when they do not in fact have disease. Hence, a method that has both sensitivity and specificity equaling one, or 100%, is preferred.

By "specifically binds," it is generally meant that an agent or polypeptide binds to a target when it binds to that target more readily than it would bind to a random, unrelated target.

"Subject" as used herein can mean a mammal that wants or is in need of the herein described compounds. The subject may be a patient. The subject may be a human or a non-human animal. The subject may be a vertebrate. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be male. The subject may be female. The subject may be of any age or stage of development, such as, for example, an adult, an adolescent, a child, or an infant. In some embodiments, the subject is human. In some embodiments, the subject has a specific genetic marker.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides.

A "therapeutically effective amount," or "effective dosage," or "effective amount" as used interchangeably herein unless otherwise defined, means a dosage of an agent, compound, or drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in a subject. A therapeutically effective amount may be administered in one or more administrations (e.g., the composition may be given as a preventative treatment or therapeutically at any stage of disease progression, before or after symptoms, and the like), applications, or dosages, and is not intended to be limited to a particular formulation, combination, or administration route. It is within the scope of the present disclosure that the agent, compound, or drug may be administered at various times during the course of treatment of the subject. The times of administration and dosages used will depend on several factors, such as the goal of treatment (e.g., treating v. preventing), condition of the subject, etc. and can be readily determined by one skilled in the art. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder, or disease. Treatment also includes prolonging survival as compared to expected survival if not receiving treatment. The terms "treat," "treated," or "treating" may include preventing, suppressing, repressing, ameliorating, or completely eliminating the disease. Preventing the disease may involve administering a composition of the present invention to a subject prior to onset of the disease. Suppressing the disease may involve administering a composition of the present invention to a subject after induction of the disease but before its clinical appearance. Repressing or ameliorating the disease may involve administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequence substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. ADIPOGENESIS

Adipogenesis is the process of cell differentiation by which pre-adipocytes become adipocytes. Pre-adipocytes are undifferentiated fibroblasts, derived from mesenchymal stem cells, that can be stimulated to form adipocytes. Adipocytes (also known as lipocytes or fat cells) are the cells that primarily compose adipose tissue. Adipose tissue (also referred to as body fat, or simply fat) is a loose connective tissue composed mostly of adipocytes. Adipocytes are specialized in storing energy as fat. If excess weight is gained as an adult, adipocytes may increase in size about four-fold before dividing and increasing the absolute number of adipocytes present. Types of adipose tissue include white adipose tissue (WAT) and brown adipose tissue (BAT). A third type of adipocyte is the beige adipocyte. In some embodiments, the size of the fat vacuole(s) depends upon the type of cell (white, versus beige, versus brown adipocyte). The lipid droplets in adipose tissue can be unilocular or multilocular. Unilocular cells contain a single large lipid droplet which pushes the cell nucleus against the plasma membrane, giving the cell a signet-ring shape. Multilocular cells contain more than one lipid droplet.

White adipose tissue (WAT) is comprised of white adipocytes. White adipocytes are monovacuolar cells. They contain a single large vacuole that comprises fat. The vacuole may also be referred to as a lipid droplet. Unilocular cells, characteristic of WAT, may range in size from about 25 microns to 200 about microns. White adipocytes may be at least about 25 microns, at least about 50 microns, at least about 75 microns, at least about 100 microns, at least about 125 microns, at least about 150 microns, or at least about 175 microns in diameter. White adipocytes may be less than about 200 microns, less than about 175 microns, less than about 150 microns, less than about 125 microns, less than about 100 microns, less than about 75 microns, or less than about 50 microns in diameter. The single large vacuole of fat is surrounded by a layer of cytoplasm. The nucleus is flattened and located on the periphery. The fat stored is in a semi-liquid state, and is composed primarily of triglycerides (TG) and cholesteryl ester. Mitochondria are found predominately in the thicker portion of the cytoplasmic rim near the nucleus. When needed, lipases may hydrolyze triglycerides of white adipocytes into fatty acids, and the fatty acids are oxidized in mitochondria to generate energy, that is, to drive ATP synthesis. WAT is capable of releasing a number of adipokines that regulate immune responses, blood pressure, angiogenesis, bone mass, and the thyroid.

Brown adipose tissue (BAT) is comprised of brown adipocytes. Brown adipocytes are plurivacuolar cells and are polygonal in shape. They contain a plurality of smaller vacuoles that comprise fat. The vacuole may also be referred to as a lipid droplet. Multilocular cells are characteristic of BAT. A cell in BAT may reach a diameter of about 60 microns, and the lipid droplet within the cell may reach about 25 microns in diameter (Albright, A. L. and Stern, J. S. (1998). Adipose tissue. In: Encyclopedia of Sports Medicine and Science, T. D. Fahey (Editor). Internet Society for Sport Science: http://sportsci.org. 30 May 1998). Brown adipocytes may be at least about 40 microns, at least about 50 microns, or at least about 60 microns in diameter. Brown adipocytes may be less than about 80 microns, less than about 70 microns, or less than about 60 microns in diameter. The lipid droplet in a brown adipocyte may be at least about 15 microns, at least about 20 microns, or at least about 25 microns in diameter. The lipid droplet in a brown adipocyte may be less than about 35 microns, less than about 30 microns, or less than about 25 microns in diameter. A brown adipocyte may have at least 2, at least 3, at least 4, at least 5, at least 6, at least 7, at least 8, at least 9, at least 10, at least 15, or at least 20 lipid droplets. Unlike white adipocytes, brown adipocytes have considerable cytoplasm, with small lipid droplets scattered throughout. The nucleus is round, and, although eccentrically located, it may not be in the periphery of the cell. The brown color comes from the large quantity of mitochondria. Brown fat, also known as "baby fat," is used to generate heat. BAT provides non-shivering thermogenesis, wherein lipases may hydrolyze triglycerides of brown adipocytes into fatty acids, and the fatty acids are oxidized in mitochondria to generate energy that is released as heat due to mitochondrial uncoupling. Mitochondrial uncoupling is a process by which electron transport is not used to drive ATP synthesis or drive net ion translocation across a membrane.

Brown-like adipocytes also occur in WAT and may be derived from WAT progenitor cells. These are "beige" adipocytes. Beige adipocytes can be found in various locations in humans and mice. Multilocular, UCP1-positive cells are prominent in the subcutaneous white adipose depots of mice and humans. Beige adipocytes are distinct from brown adipocytes and have a different lineage, and they have a gene expression pattern distinct from either white or brown adipocytes. Beige cells may have a gene expression pattern distinct from either white fat or brown fat. Beige adipocytes may have characteristics of both white and brown adipocytes. The genes differentially expressed in beige adipocytes may include, for example, Klhl13, CD40, Ear2, Tmem26, CD137, Sp100, Tbx1, or Slc27A1 (specific gene expression profiles are described in, for example, Wu, J. et al. *Cell* 2012, 150, 366-376). A beige adipocyte may be distinguished from a white adipocyte, from a brown adipocyte, or from both a white adipocyte and a brown adipocyte by determining the level of expression of a gene selected from Klhl13, CD40, Ear2, Tmem26, CD137, Sp100, Tbx1, and Slc27A1, or a combination thereof. A beige adipocyte may have a greater level of expression of a gene selected from Klhl13, CD40, Ear2, Tmem26, CD137, Sp100, Tbx1, and Slc27A1, or a combination thereof, as compared to a white adipocyte or a brown adipocyte.

Obesity is a medical condition in which excess body fat has accumulated to the extent that it may have a negative effect on health. A human subject may be considered "obese" when their body mass index (BMI) is over 30 $kg/m^2$, with the range 25-30 $kg/m^2$ defined as "overweight." "Severe obesity" is classified as a BMI greater than or equal to 35 $kg/m^2$ and less than 40 $kg/m^2$. "Morbid obesity" is classified as a BMI greater than or equal to 35 $kg/m^2$ and with obesity-related health conditions, or as a BMI greater than or equal to 40 $kg/m^2$ and less than 45 $kg/m^2$. "Super obesity" is classified as a BMI greater than or equal to 45 $kg/m^2$. BMI is a measurement obtained by dividing a subject's weight by the square of the subject's height, usually expressed in kilograms per square meter. Obesity may be further evaluated in terms of fat distribution via the waist-hip ratio and total cardiovascular risk factors. Obesity is characterized by the expansion of fat mass, through adipocyte size increase (hypertrophy) and, to a lesser extent, cell proliferation (hyperplasia). In the fat cells of obese individuals, there is increased production of metabolism modulators, such as glycerol, hormones, macrophage stimulating chemokines, and pro-inflammatory cytokines, leading to the development of insulin resistance.

a. Clk1

Dual specificity protein kinase Clk1 (also referred to as cdc2-like kinase1) is a dual specificity protein kinase. Clk1 is found in the cell nucleus and phosphorylates serine/arginine-rich proteins involved in pre-mRNA processing, releasing them into the nucleoplasm. The choice of splice sites during pre-mRNA processing may be regulated by the concentration of transacting factors, including serine/arginine-rich proteins. Clk1 may play a role in governing splice site selection. The Clk family of dual specificity protein kinases includes Clk1, Clk2, Clk3, and Clk4.

Clk1 activity may regulate terminal differentiation of adipocytes during adipogenesis through the regulation of alternative splicing of several protein splice variants. In some embodiments, Clk1 inhibition may be used to promote differentiation of a white adipocyte into a beige adipocyte. Clk1 inhibition may increase the levels of PGC1α. Clk1 inhibition may increase the levels of UCP1. Clk1 inhibition in terminal differentiation of adipocytes may promote beige adipocyte differentiation by stimulating more mitochondria to develop via elevated PGC1α, and to burn rather than store energy via increased UCP1 expression and increased fatty acid oxidation. Clk1 inhibition during adipogenesis may reprogram a new adipocyte population and circumvent their normal development to that of beige adipocytes, which burn more energy (via increased mitochondrial number and UCP1) rather than store it as triglycerides (lipid droplets) as compared to white adipocytes.

b. UCP1

Uncoupling protein 1 (UCP1), also referred to as thermogenin, is an uncoupling protein found in the mitochondria of brown adipose tissue (BAT). UCP1 is a transmembrane protein that can decrease the proton gradient generated in oxidative phosphorylation. UCP1 decreases the protein gradient by increasing the permeability of the inner mitochondrial membrane, allowing protons that have been pumped into the intermembrane space to return to the mitochondrial matrix. UCP1 in brown adipose tissue provides a mechanism for the enormous heat-generating capacity of the tissue. UCP1 may be used to generate heat by non-shivering thermogenesis.

UCP1 may be activated in the brown fat cell by fatty acids and may be inhibited by nucleotides. Fatty acids may activate UCP1 by causing the following signaling cascade: sympathetic nervous system terminals release norepinephrine onto a beta-3 adrenergic receptor on the plasma membrane; this signaling cascade may activate adenylyl cyclase, which catalyzes the conversion of ATP to cyclic AMP (cAMP); cAMP activates protein kinase A, causing its active C subunits to be freed from its regulatory R subunits; active protein kinase A, in turn, phosphorylates triacylglycerol lipase, thereby activating it; the lipase converts triacylglycerols into free fatty acids, which activate UCP1, overriding the inhibition caused by purine nucleotides (GDP and ADP). During the termination of thermogenesis, UCP1 is inactivated, and residual fatty acids are disposed of through oxidation, allowing the cell to resume its normal energy-conserving state.

Increased expression of UCP1 in adipose tissue may indicate stimulation of burning rather than storing energy, which may indicate that the tissue is becoming brown adipose tissue, or transitioning from white to beige adipose tissue.

c. PGC1α

Peroxisome proliferator-activated receptor gamma-coactivator-1-alpha (PGC1α) is a protein that is a transcriptional coactivator. PGC1α regulates genes involved in energy metabolism and is a regulator of mitochondrial biogenesis. PGC1α may interact with the nuclear receptor PPAR-γ, which permits the interaction of PGC1α with multiple transcription factors. PGC1α may interact with, and regulate the activities of, cAMP response element-binding protein (CREB) and nuclear respiratory factors (NRFs).

PGC1α may be a factor in causing slow-twitch rather than fast-twitch muscle fiber types, controlling blood pressure, regulating cellular cholesterol homoeostasis, and the development of obesity. PGC1α may increase Akt (PKB) and Phospho-Akt (Ser473 and Thr308) levels in muscle. PGC1α may lead to calcineurin activation. PGC1α may be activated by factors including, for example, reactive oxygen species (ROS) and reactive nitrogen species (RNS), both formed endogenously in the cell as by-products of metabolism but upregulated during times of cellular stress; cold exposure; endurance exercise (for example, PGC1α may determine lactate metabolism, thereby preventing high lactate levels in endurance athletes and making lactate as an energy source more efficient; cAMP response element-binding (CREB) proteins, which may be activated by an increase in cAMP following external cellular signals; and SIRT1, which binds and activates PGC1α through deacetylation inducing gluconeogenesis without affecting mitochondrial biogenesis. PGC1α may increase β-aminoisobutyric acid secretion by exercising muscles. The effect of β-aminoisobutyric acid in white adipose tissue may include the activation of thermogenic genes that prompt the browning of white adipose tissue.

Increased expression of PGC1α in adipose tissue may indicate increased development of mitochondria, which may indicate that the tissue is becoming brown adipose tissue, or transitioning from white to beige adipose tissue.

3. COMPOUNDS

Provided herein are compounds. The compound, upon administration to a subject or a cell, may elicit a variety of effects. The compounds may be used to transition or convert a white adipocyte to a beige adipocyte. The compounds may be used to transition or convert white adipose tissue to beige adipose tissue. The compound may inhibit Clk1. The compounds may be specific in targeting and inhibiting Clk1. In some embodiments, the compound binds to Clk1. In some embodiments, the compound is specific for Clk1. In some embodiments, the compound does not inhibit Clk2, Clk3, or Clk4, or a combination thereof. The compound may increase the expression of UCP1. The compound may increase the expression of PGC1α. The compound may increase the expression of UCP1 and PGC1α. The compound may increase the number of mitochondria in an adipocyte. The compound may decrease alternative splicing of a gene, such as, for example, protein kinase C beta 1 (PKCβ1). The compound may increase the number of lipid droplets in an adipocyte. The compound may increase the number of lipid droplets in an adipocyte by at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold. The compound may decrease the size of lipid droplets in an adipocyte. Size may be measured by measuring the diameter. The compound may decrease the size of a lipid droplet in an adipocyte by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. The compound may decrease the size of an adipocyte. Size may be measured by measuring the diameter. The compound may decrease the size of an adipocyte by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. The activity of the compound may be monitored and/or determined by, for example, measuring the effect of the compound on the amount of mitochondria, the size of lipid droplets, the number of lipid droplets, the size of an adipocyte, the expression of PGC1α, the expression of UCP1, or a combination thereof, in a cell. Cell lines may include 3T3-L1 cells. The level of expression of PGC1α and/or UCP1 may be determined by methods known to one of skill in the art such as, for example, Western blot analysis, Northern blot analysis, immunohistochemistry, immunoassays, and probes to mRNA. The activity of the compound can be determined by staining cells, such as adipose cells, with dyes such as Oil Red O, MitoTracker™ Green (Thermo Fischer Scientific, Waltham, Mass.) stain, or a combination thereof. A decrease in Oil Red O stain may indicate increased activity of the compound. An increase in MitoTracker™ Green (Thermo Fischer Scientific, Waltham, Mass.) stain may indicate increased activity of the compound. An increase in MitoTracker™ Green (Thermo Fischer Scientific, Waltham, Mass.) stain may indicate stimulation of mitochondrial biogenesis. An increase in mitochondrial activity may be analyzed using a respirometer such as the Seahorse Analytical or Oroborus instruments. As detailed in the Examples, molecular modeling programs were used to indicate that the compound may be specific for inhibiting Clk1 kinase. The compound may stimulate mitochondrial biogenesis at 100 nM concentrations or greater, and this stimulation may occur whether the cells are exposed to the compound for 6 days, 4 days, or 2 days. The IC50 of the compound may be roughly equal to that of TG003, which may be about 20 nM, at least about 10 nM, at least about 15 nM, less than about 30 nM, or less than about 25 nM.

The compound may be selected from the following:

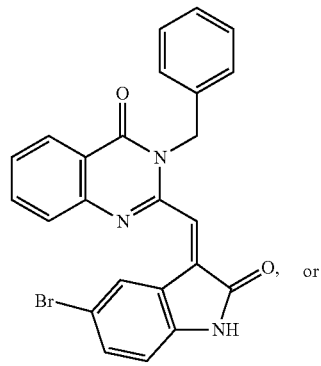

DC677

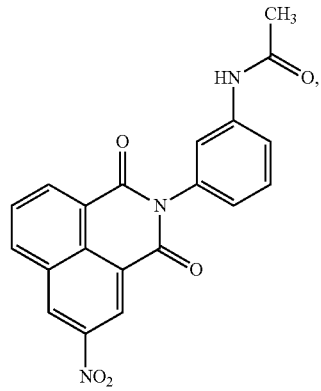

DC761 or a pharmaceutically acceptable salt thereof, or a combination thereof.

In some embodiments, the compound comprises DC677:

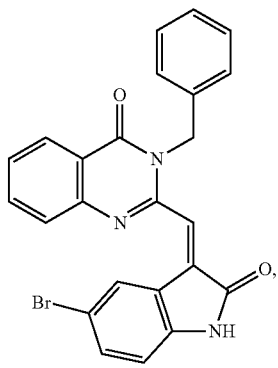

or pharmaceutically acceptable salt thereof.

In some embodiments, the compound comprises DC761:

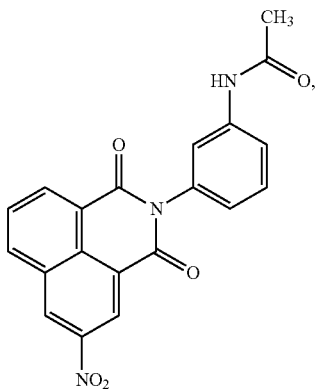

or pharmaceutically acceptable salt thereof.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45, 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those detailed herein, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds are $^{11}$C, $^{13}$N, $^{15}$O, and $^{18}$F. Isotopically-labeled compounds can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. Synthesis of Compounds

Compounds DC677 and DC761 are commercially available, for example, from Hit2Lead (ChemBridge Online Chemical Store, ChemBridge Corporation, San Diego, Calif.) as ID No. 6143677 (3-benzyl-2-[(5-bromo-2-oxo-1,2-dihydro-3H-indol-3-ylidene)methyl]-4(3H)-quinazolinone) with MW 458, and ID No. 7394761 (N-[3-(5-nitro-1,3-dioxo-1H-benzo[de]isoquinolin-2(3H)-yl)phenyl]acetamide) with MW 375, respectively. Alternatively, compounds DC677 and DC761 may be synthetically made by methods known to one of skill in the art.

c. Pharmaceutical Compositions

The compounds or salts as detailed herein may be formulated into pharmaceutical compositions accordance with standard techniques well known to those skilled in the pharmaceutical art. The composition may comprise the compound and a pharmaceutically acceptable carrier. The term "pharmaceutically acceptable carrier," as used herein, means a non-toxic, inert solid, semi-solid or liquid filler, diluent, encapsulating material or formulation auxiliary of any type.

The route by which the disclosed compounds are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). In some embodiments, the pharmaceutical composition is for administration to a subject's central nervous system. Techniques and formulations may generally be found in "Remington's Pharmaceutical Sciences," (Meade Publishing Co., Easton, Pa.). Pharmaceutical compositions must typically be sterile and stable under the conditions of manufacture and storage. All carriers are optional in the compositions.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of lubricant(s) in a systemic or topical composition may typically be about 5 to about 10%.

Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition may typically be about 0.1 to about 10%.

Suitable colorants include, for example, a colorant such as an FD&C dye. When used, the amount of colorant in a systemic or topical composition may typically be about 0.005 to about 0.1%.

Suitable flavors include, for example, menthol, peppermint, and fruit flavors. The amount of flavor(s), when used, in a systemic or topical composition may typically be about 0.1 to about 1.0%.

Suitable sweeteners include, for example, aspartame and saccharin, or a combination thereof. The amount of sweetener(s) in a systemic or topical composition may typically be about 0.001 to about 1%.

Suitable antioxidants include, for example, butylated hydroxyanisole ("BHA"), butylated hydroxytoluene ("BHT"), and vitamin E. The amount of antioxidant(s) in a systemic or topical composition may typically be about 0.1 to about 5%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, Pa.) and sodium alginate. The amount of suspending agent(s) in a systemic or topical composition may typically be about 1 to about 8%.

Suitable surfactants include, for example, lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a topical composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may typically be 0% to 95%.

Suitable pH adjusting additives include, for example, HCl or NaOH in amounts sufficient to adjust the pH of a topical pharmaceutical composition.

In some embodiments, the pharmaceutically acceptable carrier is a sugar such as lactose, glucose, and sucrose. In some embodiments, the pharmaceutically acceptable carrier is a starch such as, for example, corn starch and potato starch. In some embodiments, the pharmaceutically acceptable carrier is cellulose and its derivatives such as, but not limited to, sodium carboxymethyl cellulose, ethyl cellulose and cellulose acetate. In some embodiments, the pharmaceutically acceptable carrier is powdered tragacanth, malt, gelatin, or talc. In some embodiments, the pharmaceutically acceptable carrier is an excipient such as, but not limited to, cocoa butter and suppository waxes. In some embodiments, the pharmaceutically acceptable carrier is oil such as, but not limited to, peanut oil, cottonseed oil, safflower oil, sesame oil, olive oil, corn oil and soybean oil. In some embodiments, the pharmaceutically acceptable carrier is a glycol, such as propylene glycol. In some embodiments, the pharmaceutically acceptable carrier is an ester such as, but not limited to, ethyl oleate and ethyl laurate. In some embodiments, the pharmaceutically acceptable carrier is an agar. In some embodiments, the pharmaceutically acceptable carrier is a buffering agent such as, but not limited to, magnesium hydroxide and aluminum hydroxide. In some embodiments, the pharmaceutically acceptable carrier is alginic acid, pyrogen-free water, isotonic saline, Ringer's solution, ethyl alcohol, or a phosphate buffer solution. In some embodiments, the pharmaceutically acceptable carrier is a non-toxic compatible lubricant such as, but not limited to, sodium lauryl sulfate and magnesium stearate.

Compositions for oral administration can have various dosage forms. For example, solid forms include tablets, capsules, granules, and bulk powders. Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Capsules (including implants, time release, and sustained release formulations) typically include a compound, and a carrier including one or more diluents disclosed above in a capsule comprising gelatin. Granules typically comprise a compound, and preferably glidants such as silicon dioxide to improve flow characteristics. Implants can be of the biodegradable or the non-biodegradable type.

Compositions for oral administration can have solid forms. Solid oral compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Compositions for topical administration can be applied locally to the skin and may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compounds into the skin. In the topical compositions, the carrier includes a topical carrier. Suitable topical carriers can include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications may include propylene glycol, dimethyl isosorbide, and water, and even more particularly, phosphate buffered saline, isotonic water, deionized water, monofunctional alcohols, and symmetrical alcohols. The carrier of a topical composition may further include one or more ingredients selected from emollients, propellants, solvents, humectants, thickeners, powders, fragrances, pigments, and preservatives, all of which are optional.

Although the amounts of components in the compositions may vary depending on the type of composition prepared, in general, systemic compositions may include 0.01% to 50% of a compound and 50% to 99.99% of one or more carriers. Compositions for parenteral administration may typically include 0.1% to 10% of compound and 90% to 99.9% of one or more carriers. Oral dosage forms may include, for example, at least about 5%, or about 25% to about 50% of compound. The oral dosage compositions may include about 50% to about 95% of carriers, or from about 50% to about 75% of carriers. The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

d. Administration

The compounds or salts as detailed herein, or the pharmaceutical compositions comprising the same, may be administered to a subject. Such compositions comprising a compound can be administered in dosages and by techniques well known to those skilled in the medical arts taking into consideration such factors as the age, sex, weight, and condition of the particular subject, and the route of administration.

The compound can be administered prophylactically or therapeutically. In prophylactic administration, the compound can be administered in an amount sufficient to induce a response. In therapeutic applications, the compounds are administered to a subject in need thereof in an amount sufficient to elicit a therapeutic effect. An amount adequate to accomplish this is defined as "therapeutically effective amount." Amounts effective for this use will depend on, e.g., the particular composition of the compound regimen administered, the manner of administration, the stage and severity of the disease, the general state of health of the patient, and the judgment of the prescribing physician. A therapeutically effective amount is also one in which any toxic or detrimental effects of a compound of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg (mg of compound per kg of subject).

The compound can be administered by methods well known in the art as described in Donnelly et al. (Ann. Rev. Immunol. 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The compound can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The compound can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the compound is administered intravenously, intraarterially, or intraperitoneally to the subject. In some embodiments, the compound is administered to the central nervous system of the subject.

4. METHODS a. Methods of Inhibiting Clk1

Provided herein are methods of inhibiting Clk1 in a subject in need thereof. The method may include administering to the subject a compound or pharmaceutical composition as detailed herein. In some embodiments, the compound does not inhibit Clk2, Clk3, or Clk4, or a combination thereof. In some embodiments, the lipid droplets of the adipocytes in the subject are reduced in size relative to a control. In some embodiments, the adipocytes in the subject store less lipids relative to a control. In some embodiments, the expression of UCP1 in the subject is increased relative to a control. In some embodiments, the expression of PGCα in the subject is increased relative to a control. In some embodiments, the expression levels of UCP1 and PGCα in the subject are increased relative to a control. In some embodiments, the control comprises white adipocytes. In some embodiments, the control comprises a sample from the subject prior to administration of the compound or pharmaceutical composition.

b. Methods of Reducing or Treating Obesity

Provided herein are methods of reducing or treating obesity in a subject. The method may include administering to the subject a compound or pharmaceutical composition as detailed herein. In some embodiments, Clk1 is inhibited. In some embodiments, Clk2, Clk3, Clk4, or a combination thereof, is not inhibited. In some embodiments, the lipid droplets of the adipocytes in the subject are reduced in size relative to a control. In some embodiments, the adipocytes in the subject store less lipids relative to a control. In some embodiments, the expression of UCP1 in the subject is increased relative to a control. In some embodiments, the expression of PGCα in the subject is increased relative to a control. In some embodiments, the expression levels of UCP1 and PGCα in the subject are increased relative to a control. In some embodiments, the control comprises white adipocytes. In some embodiments, the control comprises a sample from the subject prior to administration of the compound or pharmaceutical composition.

c. Methods of Reducing Body Mass Index (BMI)

Provided herein are methods of reducing body mass index (BMI) in a subject. The method may include administering to the subject a compound or pharmaceutical composition as detailed herein. In some embodiments, Clk1 is inhibited. In some embodiments, Clk2, Clk3, Clk4, or a combination thereof, is not inhibited. In some embodiments, the lipid droplets of the adipocytes in the subject are reduced in size relative to a control. In some embodiments, the adipocytes in the subject store less lipids relative to a control. In some embodiments, the expression of UCP1 in the subject is increased relative to a control. In some embodiments, the expression of PGCα in the subject is increased relative to a control. In some embodiments, the expression levels of UCP1 and PGCα in the subject are increased relative to a control. In some embodiments, the control comprises white adipocytes. In some embodiments, the control comprises a sample from the subject prior to administration of the compound or pharmaceutical composition.

d. Methods of Differentiating a White Adipocyte into a Beige Adipocyte

Provided herein are methods of differentiating or converting a white adipocyte into a beige adipocyte. The method may include administering to the adipocyte a compound or pharmaceutical composition as detailed herein. In some embodiments, Clk1 is inhibited in the adipocyte. In some embodiments, Clk2, Clk3, Clk4, or a combination thereof, is not inhibited in the adipocyte. In some embodiments, the lipid droplets in the adipocyte are reduced in size relative to a control. In some embodiments, the adipocyte stores less lipids relative to a control. In some embodiments, the expression of UCP1 in the adipocyte is increased relative to a control. In some embodiments, the expression of PGCα in the adipocyte is increased relative to a control. In some embodiments, the expression levels of UCP1 and PGCα in the adipocyte are both increased relative to a control. In some embodiments, the control comprises white adipocytes.

5. EXAMPLES

Example 1

Clk1 Specific Inhibitors

Separate crystal structures for each of Clk1, Clk2, and Clk3 were prepared and minimized using Schrodinger Protein Preparation Wizard. A separate crystal structure for Clk4 was prepared and minimized using both PRIME and Protein Preparation Wizard, as Clk4 does not have a published crystal structure. Schrodinger GLIDE was used to dock these four crystal structures, and lists were made of the results. These results were then analyzed to determine the compounds that scored well (lower delta G) on Clk1 and that scored poorly on the Clk2, Clk3, and Clk4 models (higher delta G). These compounds were then scrutinized for their ability to permeate the cell and for general properties as potential pharmaceutical agents. Two compounds were determined to be suitable for biological testing, DC677 and DC761.

Example 2

Effect of Compound 1 on 3T3-L1 Cells

Figure 1B:
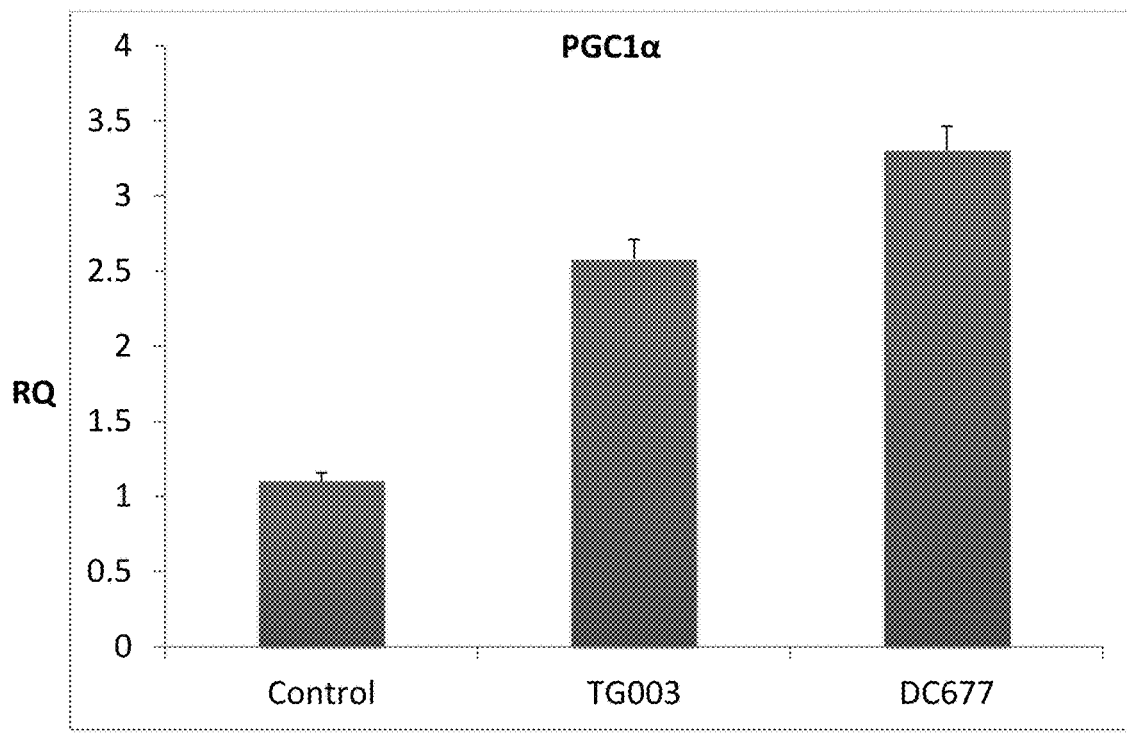
Figure 1C:
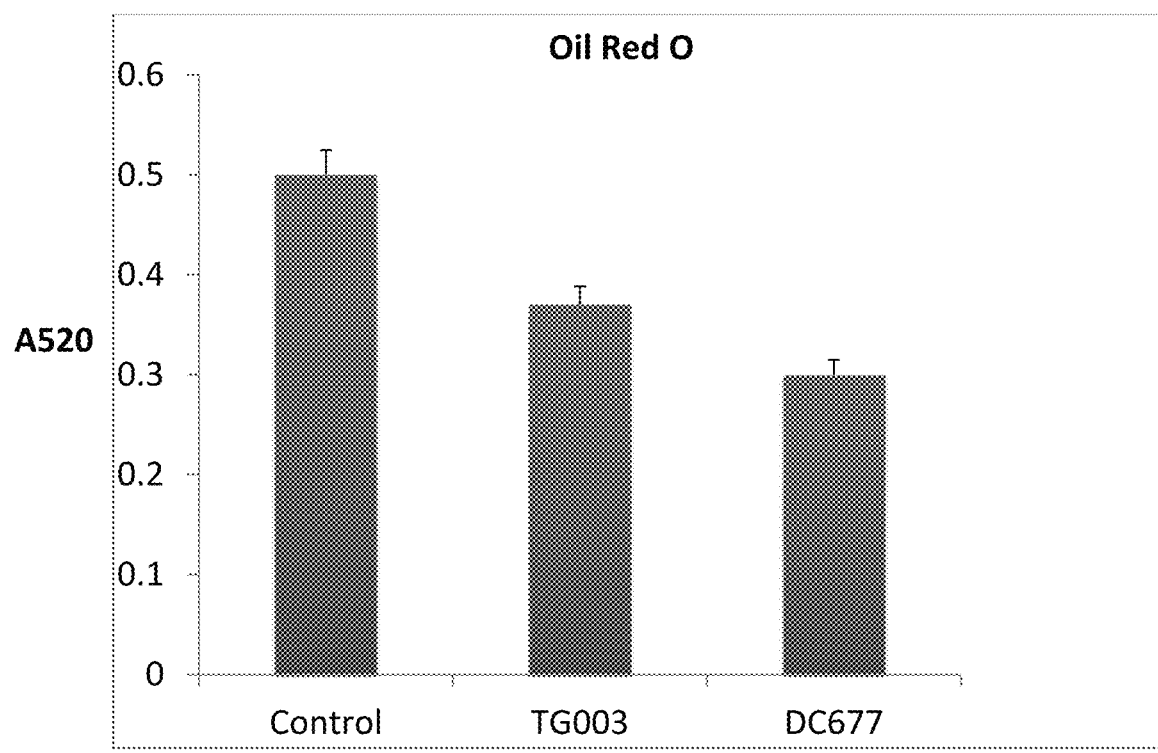
Figure 1D:
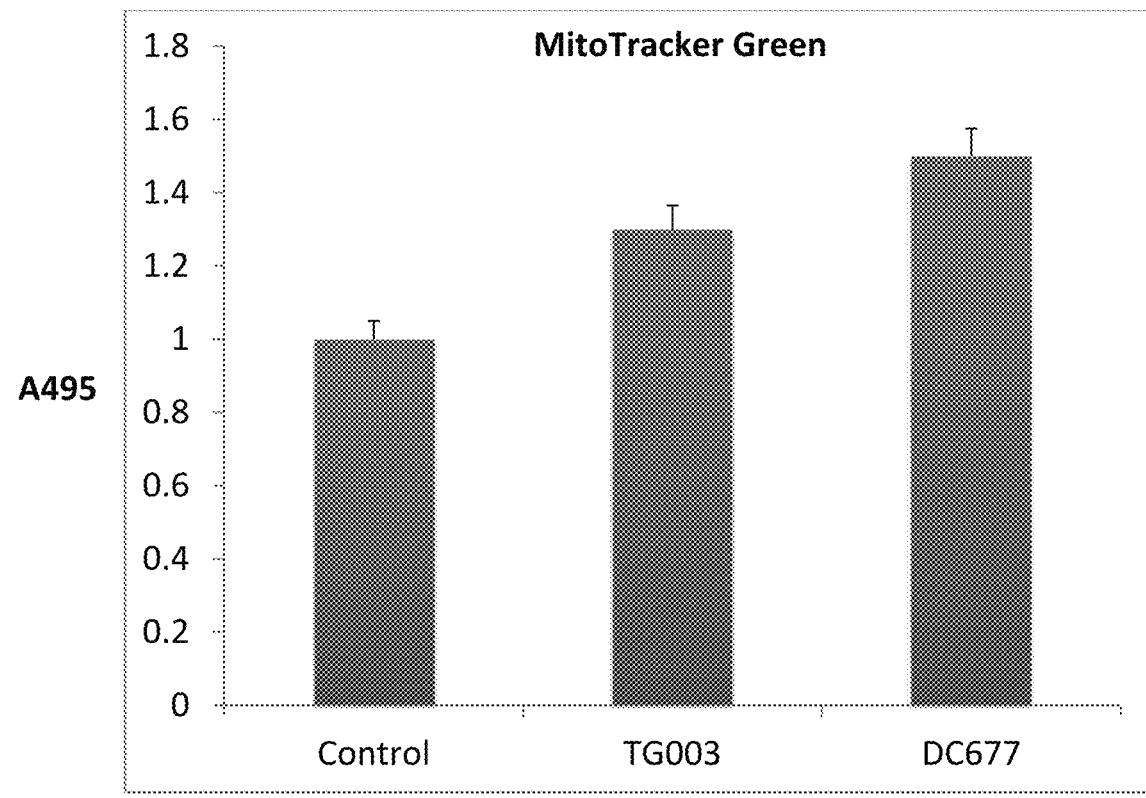
Figure 2A:
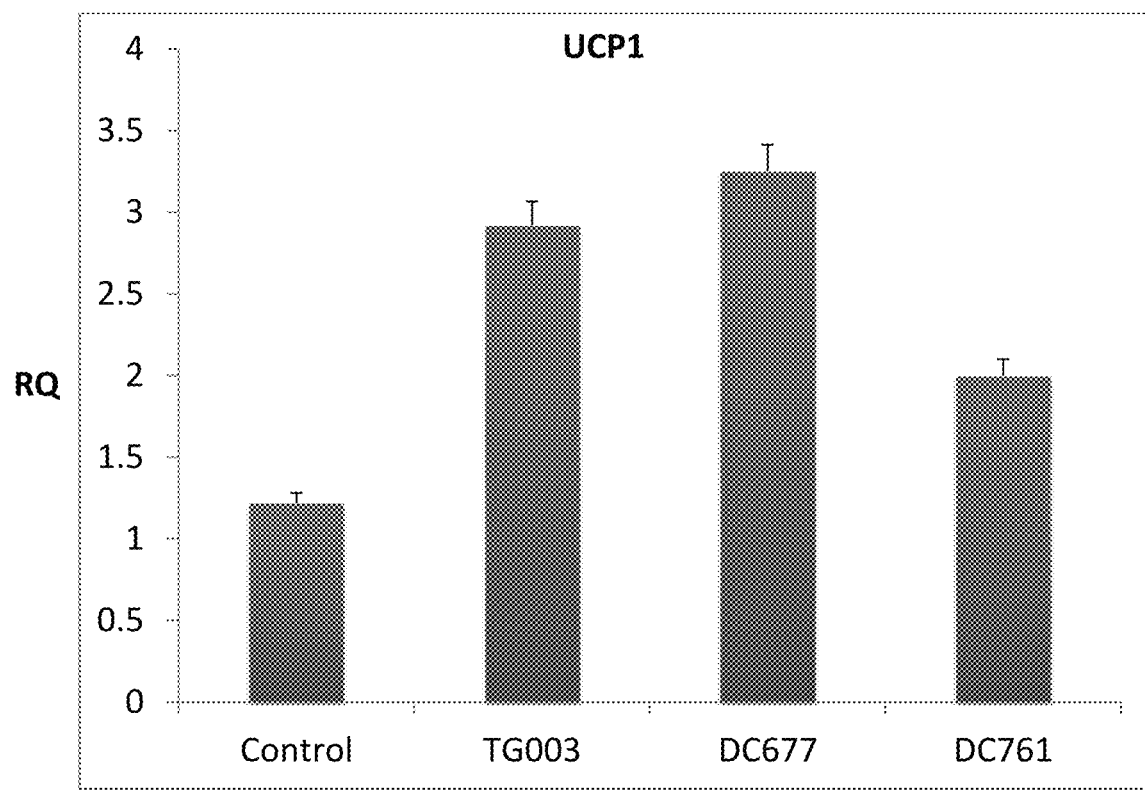
FIG. 2A, FIG. 2B, FIG. 2C, and FIG. 2D are graphs showing the effect of TG003, DC677, or DC761 on 3T3-L1 cells.
Figure 2B:
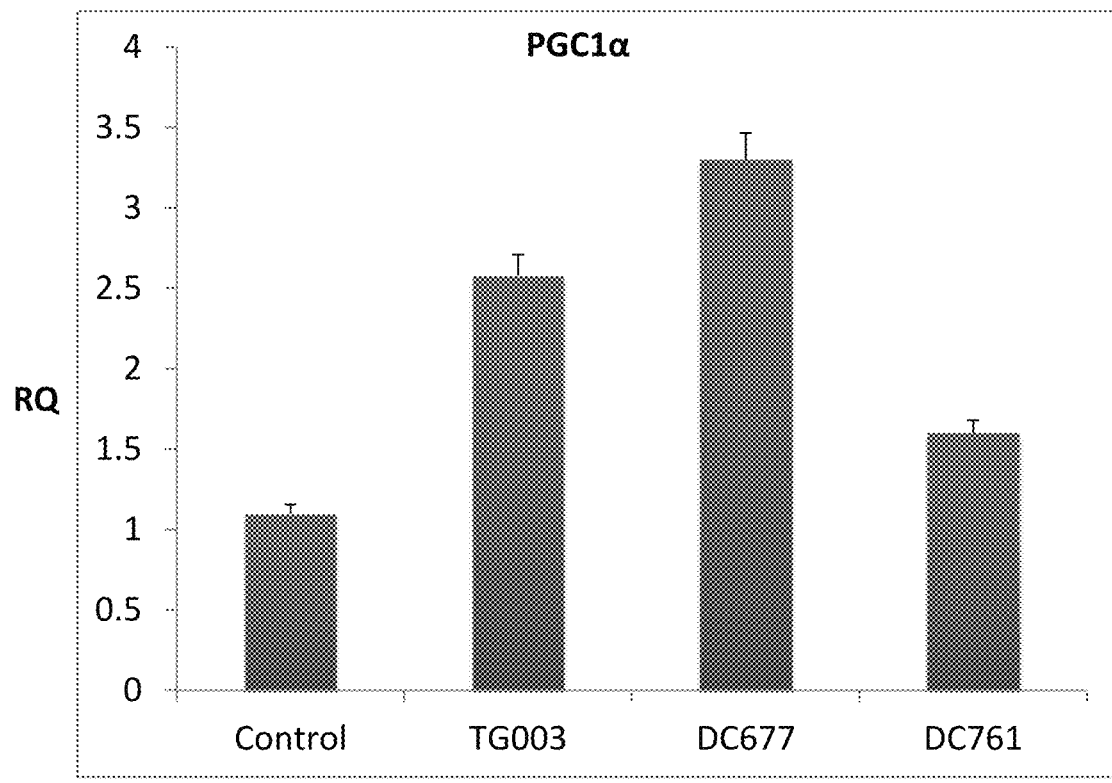
Figure 2C:
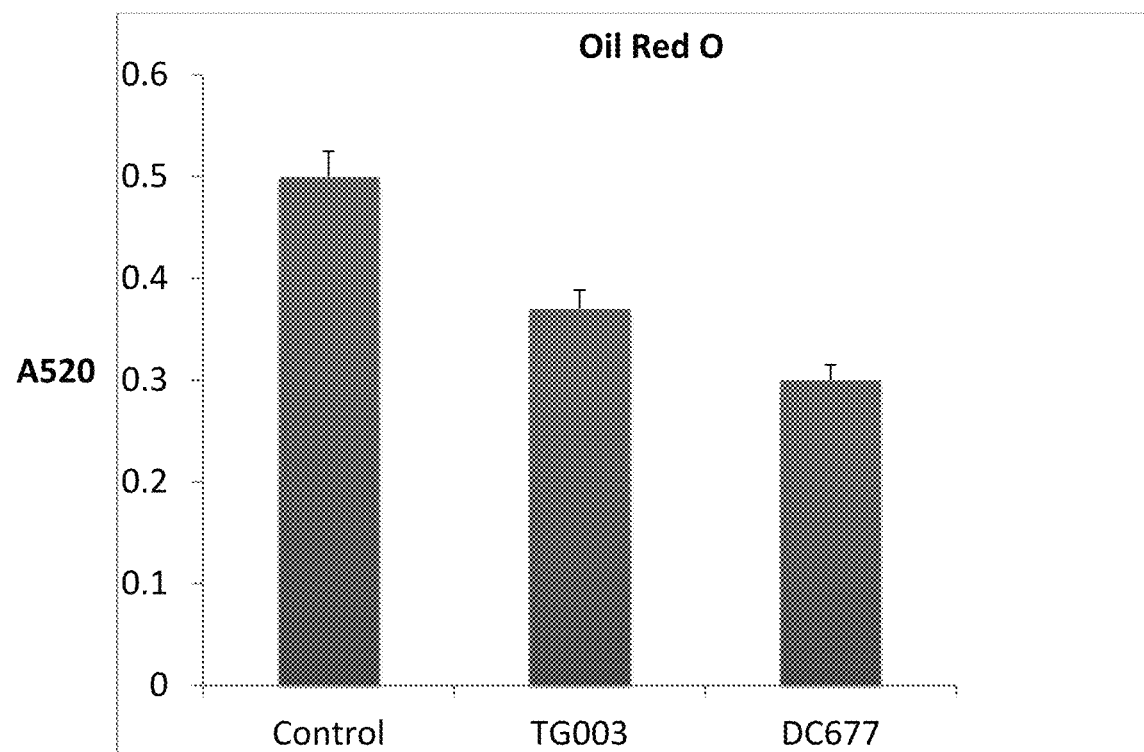
Figure 2D:
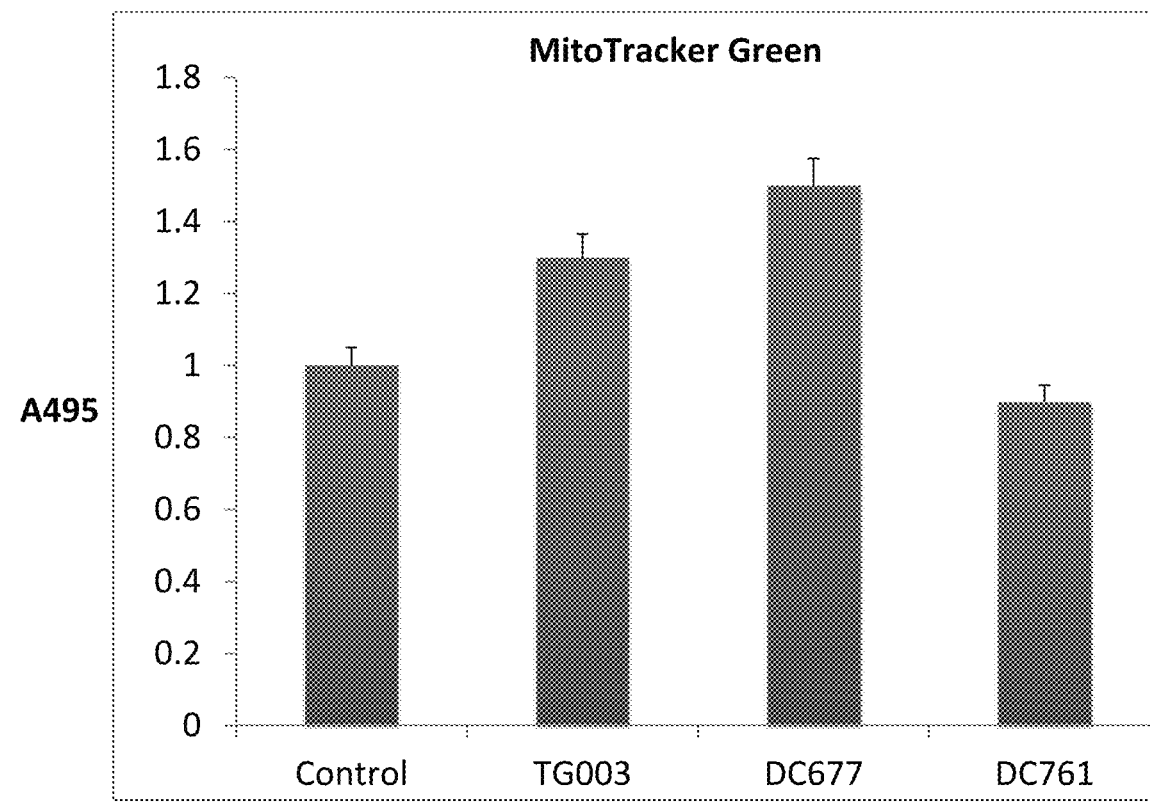

The effect of the Clk1 inhibitor DC677 or DC761 on 3T3-L1 cells was examined. 3T3-L1 cells were incubated with 50 nM TG003 (an inhibitor of Clk1), 100 nM DC677, or 100 nM DC761 for 3 to 5 days. Adipocytes were used as a control. UCP1 expression was determined (results are shown in FIG. 1A and FIG. 2A; RQ is reference quotient). PGC1α expression was determined (results are shown in FIG. 1B and FIG. 2B). Oil Red O (obtained from Sigma-Aldrich, St. Louis, Mo.) was used to stain triglycerides and lipids, and the levels of Oil Red O were determined by measuring absorbance at 520 nm (results are shown in FIG. 1C and FIG. 2C). MitoTracker™ Green (Thermo Fischer Scientific, Waltham, Mass.) was used to stain mitochondria, and levels were determined by measuring absorbance at 495 nm (results are shown in FIG. 1D and FIG. 2D).

The results indicate that 3T3-L1 cells can differentiate into "beige" cells with an inhibitor of Clk1 kinase such as DC677 or DC761. Clk1 is an enzyme that promotes alternative splicing. When treated with nanomolar concentrations of the inhibitor DC677 or DC761 for 3 to 5 days during terminal differentiation, the cells had increased UCP1 and PGC1α expression. The cells also stored fewer lipids in smaller lipid droplets that distinguish them as becoming "brown-like." The Clk1 inhibitor may induce beiging of adipocytes and switch the cell from a white to a brown-like or beige adipocyte. UCP1 is associated with adaptive non-shivering thermogenesis. "Beige" adipocytes block diet-induced obesity. By blocking alternative splicing of certain proteins in precursor cells of WAT, "beige" adipocytes may become differentiated in WAT. The results demonstrate that DC677 performs equally well to TG003, which is a standard or control inhibitor for Clk1. We conclude that the Clk inhibitors can promote mitochondrial biogenesis with only a 2 day exposure, although a longer exposure time such as 5 days is effective as well. The dose of 100 nM for DC677 demonstrates it is highly effective compared to TG003 at 50 nM. Hence, the effects of Clk1 inhibition on mitochondrial biogenesis can occur during the last phases of in vitro adipogenesis and may only require that the pre-adipocytes have been committed to differentiate on Day 3.

Figure 3:
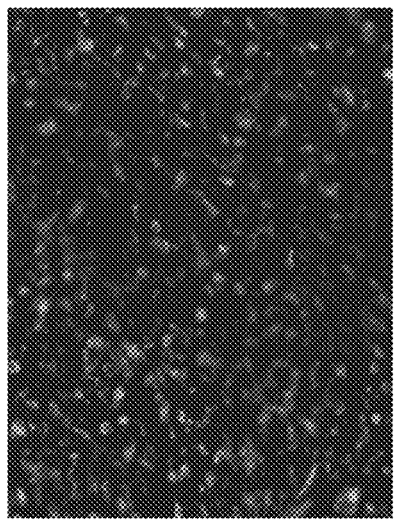
FIG. 3 are images of 3T3-L1 cells cultured in the presence of 50 nM TG003 or 100 nM DC677 at various time points and then stained with MitoTracker™ Green (Thermo Fischer Scientific, Waltham, Mass.).
Figure 3:
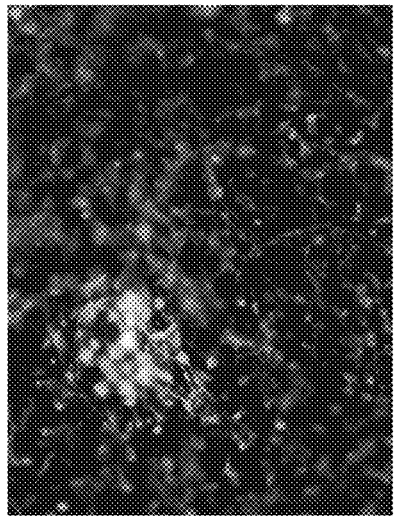
Figure 3:
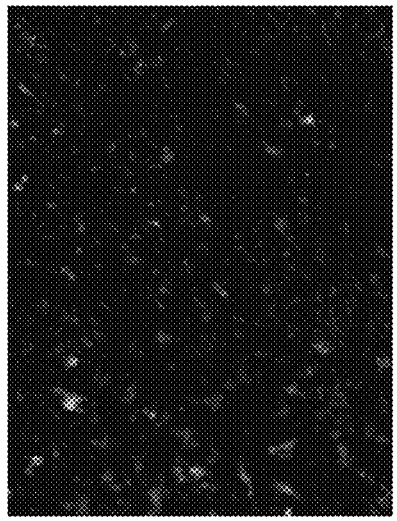
Figure 3:
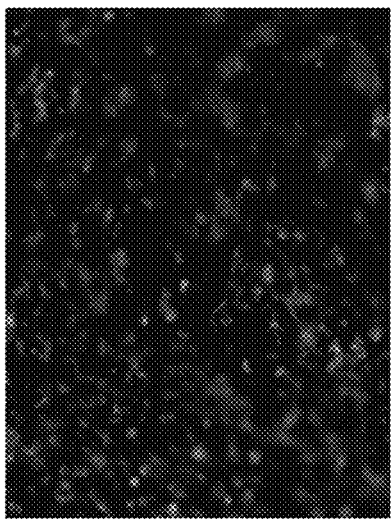
Figure 3:
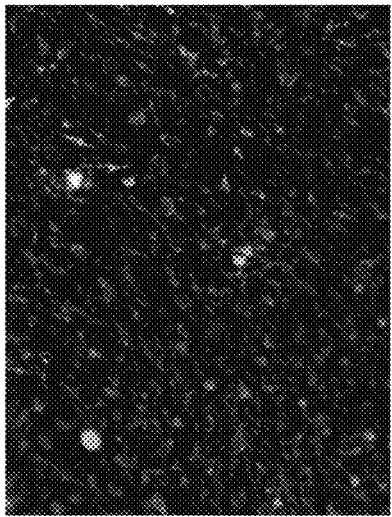
Figure 3:
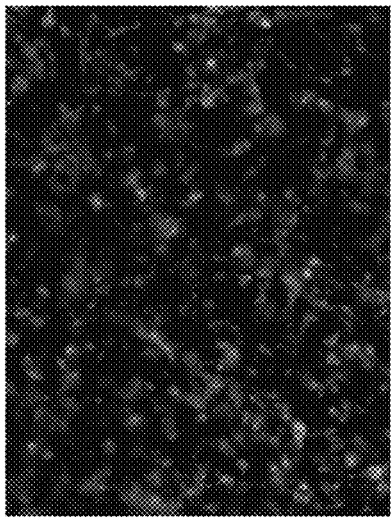

The effect of the Clk1 inhibitor DC677 on 3T3-L1 cells was examined with fluorescence microscopy. 3T3-L1 cells were cultured in a 12-well plate and differentiated by monocyte-inducing factors (MDI). The cells were then incubated with insulin, TG003, or DC677. On day 8, the cells were stained with MitoTracker™ Green (Thermo Fischer Scientific, Waltham, Mass.). Results are shown in FIG. 3. In FIG. 3, the cell treatment is as follows: (1) insulin as a control; (2) 50 nm TG003 added on day 2; (3) 50 nm TG003 added on day 4; (4) 100 nm DC677 added on day 2; (5) 100 nm DC677 added on day 4; and (6) 100 nm DC677 added on day 6.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of inhibiting Clk1 in a subject in need thereof, the method comprising administering to the subject a compound selected from the following:

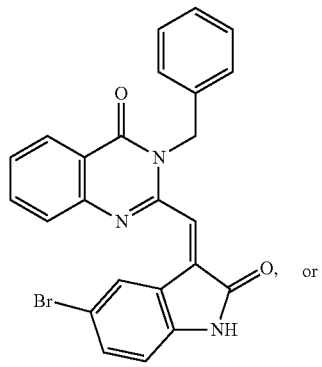

DC677 or

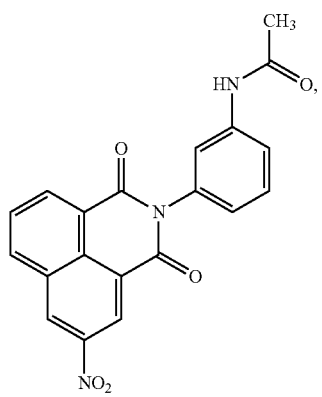

DC761 or a pharmaceutically acceptable salt thereof, or a combination thereof.

Clause 2. A method of reducing or treating obesity in a subject, the method comprising administering to the subject a compound selected from the following:

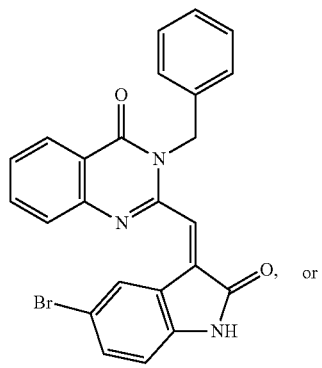

DC677 or

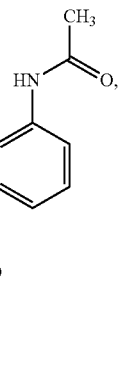

DC761 or a pharmaceutically acceptable salt thereof, or a combination thereof.

Clause 3. A method of reducing body mass index (BMI) in a subject, the method comprising administering to the subject a compound selected from the following:

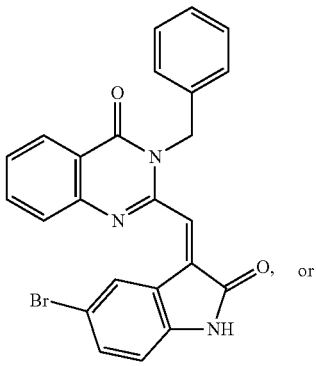

DC677 or

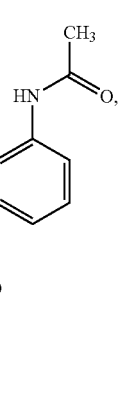

DC761 or a pharmaceutically acceptable salt thereof, or a combination thereof.

Clause 4. A method of converting a white adipocyte into a beige adipocyte, the method comprising administering to the white adipocyte a compound selected from the following:

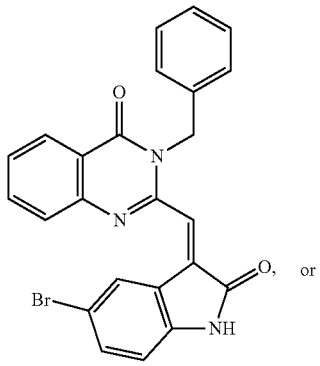
DC677

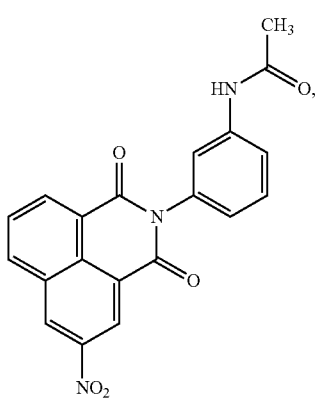
DC761 or a pharmaceutically acceptable salt thereof, or a combination thereof.

Clause 5. The method of any one of clauses 1-4, wherein the compound comprises the following:

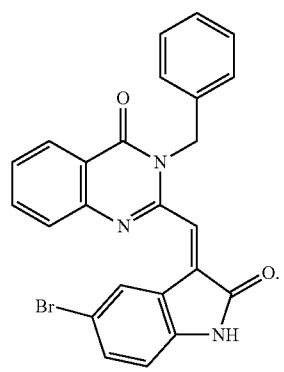 [SMILES: O=C1Nc2ccc(Br)cc2/C1=C\c1nc2ccccc2c(=O)n1Cc1ccccc1]
DC677

Clause 6. The method of any one of clauses 1-4, wherein the compound comprises the following:

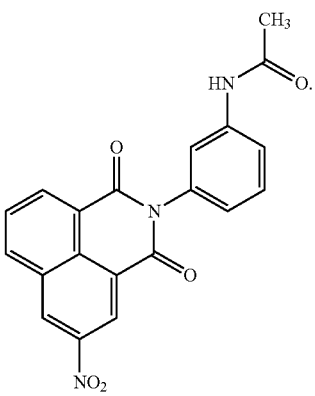 [SMILES: CC(=O)Nc1cccc(N2C(=O)c3cccc4cc([N+](=O)[O-])cc(c34)C2=O)c1]
DC761

Clause 7. The method of any one of clauses 2-4, wherein the compound or salt inhibits Clk1.

Clause 8. The method of any one of clauses 1-6, wherein the compound or salt does not inhibit Clk2, Clk3, or Clk4, or a combination thereof.

Clause 9. The method of any one of clauses 1-6, wherein the compound or salt binds to Clk1.

Clause 10. The method of any one of clauses 1-9, wherein alternative splicing of protein kinase C beta 1 (PKCβ1) is reduced relative to a control.

Clause 11. The method of any one of clauses 1-9, wherein the lipid droplets of the adipocytes in the subject are reduced in size relative to a control.

Clause 12. The method of any one of clauses 1-9, wherein the adipocytes in the subject store less lipids relative to a control.

Clause 13. The method of any one of clauses 1-9, wherein the expression of UCP1 in the subject is increased relative to a control.

Clause 14. The method of any one of clauses 1-9, wherein the expression of PGCα in the subject is increased relative to a control.

Clause 15. The method of any one of clauses 1-9, wherein the expression levels of UCP1 and PGCα in the subject are increased relative to a control.

Clause 16. The method of any one of clauses 10-15, wherein the control comprises white adipocytes.

Clause 17. The method of any one of clauses 10-15, wherein the control comprises a sample from the subject prior to administration of the compound.

Clause 18. A pharmaceutical composition comprising a compound selected from the following:

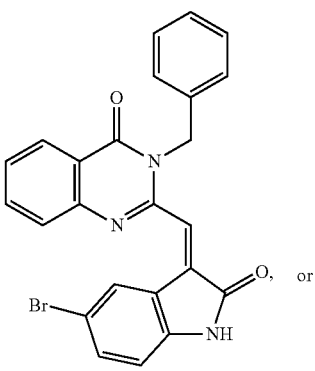
DC677

-continued

DC761

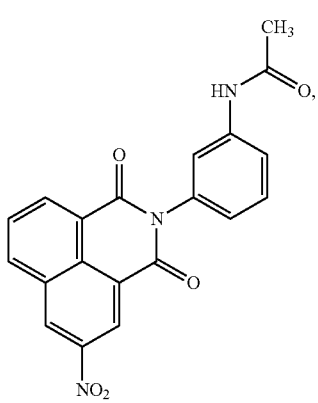

or
a pharmaceutically acceptable salt thereof, or a combination thereof, and a carrier.

Clause 19. The composition of clause 18, wherein the compound or salt inhibits Clk1.

Clause 20. The composition of clause 18 or 19, wherein the compound or salt does not inhibit Clk2, Clk3, or Clk4, or a combination thereof.

The invention claimed is:

1. A pharmaceutical composition comprising a compound selected from the following:

DC677

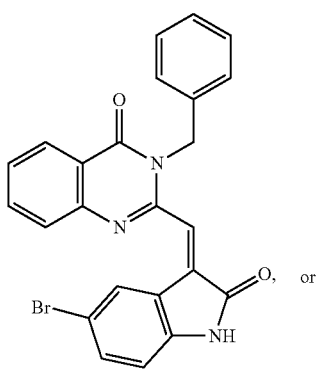

DC761 a pharmaceutically acceptable salt thereof, or a combination thereof, and a carrier.

2. The pharmaceutical composition of claim 1, wherein the compound comprises

DC677

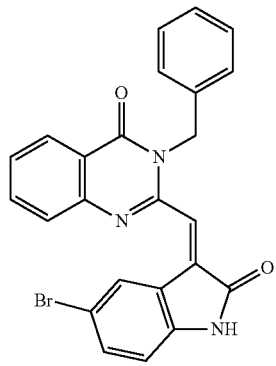

or a pharmaceutically acceptable salt thereof, or a combination thereof, and a carrier.

3. The pharmaceutical composition of claim 1, wherein the compound is

DC761

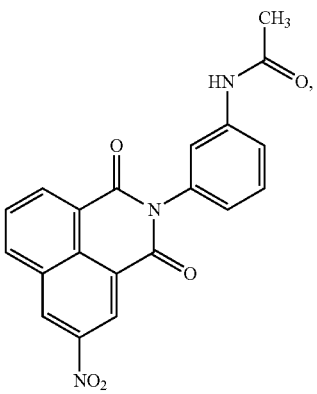

a pharmaceutically acceptable salt thereof, or a combination thereof, and a carrier.

* * * * *

UNITED STATES PATENT AND TRADEMARK OFFICE
CERTIFICATE OF CORRECTION

PATENT NO. : 10,675,283 B2  
APPLICATION NO. : 15/936326  
DATED : June 9, 2020  
INVENTOR(S) : Denise Ratzlaff Cooper et al.

Page 1 of 1

It is certified that error appears in the above-identified patent and that said Letters Patent is hereby corrected as shown below:

In the Claims

Column 35, Line 47 (Approx.), in Claim 1, after " 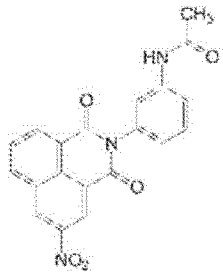 " insert --or--.

Column 36, Line 39 (Approx.), in Claim 3, after " 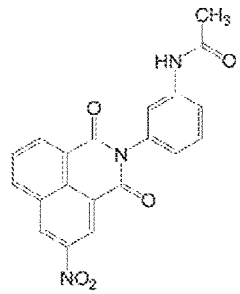 " insert --or--.

Signed and Sealed this  
Fifteenth Day of September, 2020

Andrei Iancu  
*Director of the United States Patent and Trademark Office*